(12) United States Patent
Pflaum

(10) Patent No.: US 7,078,558 B1
(45) Date of Patent: *Jul. 18, 2006

(54) CRYSTALS OF THE SODIUM SALT OF PRAVASTATIN

(75) Inventor: Zlatko Pflaum, Domzale (SI)

(73) Assignee: Lek Pharmaceutical and Chemical Company D.D., Ljubjana (SI)

( * ) Notice: Subject to any disclaimer, the term of this patent is extended or adjusted under 35 U.S.C. 154(b) by 0 days.

This patent is subject to a terminal disclaimer.

(21) Appl. No.: 10/049,093

(22) PCT Filed: Aug. 4, 2000

(86) PCT No.: PCT/IB00/01103

§ 371 (c)(1),
(2), (4) Date: Apr. 22, 2002

(87) PCT Pub. No.: WO01/10813

PCT Pub. Date: Feb. 15, 2001

(30) Foreign Application Priority Data

Aug. 6, 1999 (SI) ................................. 9900191

(51) Int. Cl.
*C07C 67/02* (2006.01)
*C07C 69/74* (2006.01)
(52) U.S. Cl. ........................ 560/119; 560/256
(58) Field of Classification Search .............. 560/256, 560/187, 188, 124, 123, 122, 119; 514/460
See application file for complete search history.

(56) References Cited

U.S. PATENT DOCUMENTS 6,740,775 B1 * 5/2004 Pflaum ...................... 560/256
2002/0081675 A1 * 6/2002 Jekkel et al. .............. 435/135

FOREIGN PATENT DOCUMENTS

WO    WO 98/45410    * 10/1998
WO    WO 00/17150      3/2000

OTHER PUBLICATIONS

Arai et al, (1988) Annu. Rep. Sankyo, 40, pp. 1-38.*

(Continued)

*Primary Examiner*—Cecilia J. Tsang
*Assistant Examiner*—Taylor Victor Oh
(74) *Attorney, Agent, or Firm*—Cohen, Pontani, Lieberman & Pavane

(57) ABSTRACT

Lovastatin, pravastatin, simvastatin, mevastatin, atorvastatin, fluvastatin and cervastatin and derivatives and analogs thereof are known as HMG-CoA reductase inhibitors and are used as antihypercholesterolemic agents. The majority of them are produced by fermentation using microorganisms of different species identified as species belonging to an *Aspergillus, Monascus, Nocardia, Amycolatopsis, Mucor*, or *Penicillium* genus, some are obtained by treating the fermentation products using the methods of chemical synthesis (simvastatin) or they are the products of total chemical synthesis (fluvastatin, atorvastatin and cervastatin). The present invention relates to a crystalline form of the sodium salt of pravastatin, which is known by the chemical name 1-naphthaleneheptanoic acid, 1,2,6,7,8,8a-hexahydro-β,δ,6-trihydroxy-2-methyl-8-(2-methyl-1-oxobutoxy)-, mono sodium salt, which is useful as a pharmaceutical substance. The present invention further relates to the method for its preparation and isolation, to a pharmaceutical formulation containing the sodium salt of pravastatin in the crystalline form and a pharmaceutically acceptable carrier, and to a pharmaceutical method of treatment. The novel crystalline form of the sodium salt of pravastatin is useful in the treatment of hypercholesterolemia and hyperlipidemia.

23 Claims, 4 Drawing Sheets

OTHER PUBLICATIONS

Figure 1:
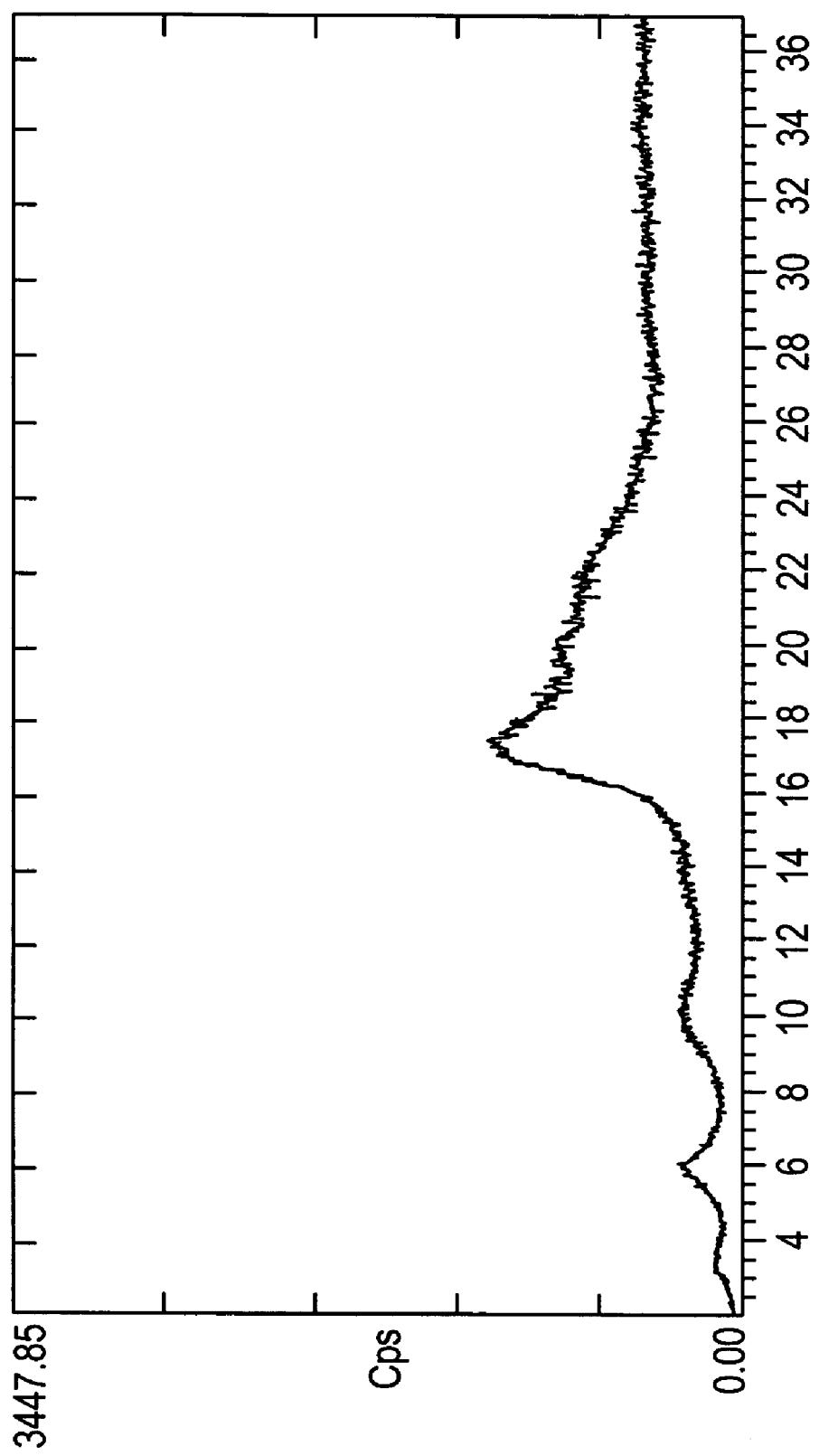

Harry G. Brittain, Polymorphism in Pharmaceutical Solids, Marcel Dekker, Inc. 1999, p. 236, lines 17-22.*

Sato et al, The Jrnl of Antibiotics vol. XLI, No. pp. 126567 (1988).

Arai et al, Pravastatin Sodium(CS 5145)—A Novel Cholesterol Lowering Agent Which Inhibits HMG-CoA Reductase (1988).

* cited by examiner

CRYSTALS OF THE SODIUM SALT OF PRAVASTATIN

The present invention relates to a crystalline form of the sodium salt of pravastatin, which is known by the chemical name 1-naphthaleneheptanoic acid, 1,2,6,7,8,8a-hexahydro-β,δ,6-trihydroxy-2-methyl-8-(2-methyl-1-oxobutoxy)-, mono sodium salt, which is useful as a pharmaceutical substance. The present invention further relates to the method for its preparation and isolation, to a pharmaceutical formulation containing the sodium salt of pravastatin in the crystalline form and a pharmaceutically acceptable carrier, and to a pharmaceutical method of treatment.

The present invention relates to a crystalline form of the sodium salt of pravastatin, which is known by the chemical name 1-naphthaleneheptanoid acid, 1,2,6,7,8,8a-hexahydro-β,δ,6-trihydroxy-2-methyl-8-(2-methyl-1-oxobutoxy)-, mono sodium salt, which is useful as a pharmaceutical substance. The present invention further relates to the method for its preparation and isolation, to a pharmaceutical formulation containing the sodium salt of pravastatin in the crystalline form and a pharmaceutically acceptable carrier, and to the pharmaceutical method of treatment.

Lovastatin, pravastatin, simvastatin, mevastatin, atorvastatin, fluvastatin and cervastatin and derivatives and analogs thereof are known as HMG-CoA reductase inhibitors and are used as antihypercholesterolemic agents. The majority of them are produced by fermentation using microorganisms of different species identified as species belonging to *Aspergillus, Monascus, Nocardia, Amycolatopsis, Mucor* or *Penicillium* genus, some are obtained by treating the fermentation products using the methods of chemical synthesis (simvastatin) or they are the products of total chemical synthesis (fluvastatin, atorvastatin and cervastatin).

Processes for the preparation of the sodium salt of pravastatin in a solid form known from the prior art comprise, for example, the step of lyophilisation. After lyophilisation only the solvent is removed but impurities remain together with the sodium salt of pravastatin. Apart from the aforementioned, lyophilisation is not very economical in large-scale production operations. During precipitation due to nonselectivity of the process, impurities precipitate together with the desired substance. Compared to the both aforementioned processes for the preparation of pharmaceutical substances in the solid form, crystallization is the only selective process wherein the molecules of the desired substance are selectively incorporated into the crystal matrix. Possibility of inclusion of impurities into the crystal is minimal because only small size molecules are able to incorporate into intermolecular space inside a crystal (related impurities, which are usually within the desired substance size range may only be incorporated into this space with great difficulty), incorporation of other molecules into the crystal matrix is not favoured thermodynamically.

The advantage of substances in the crystal structures over those in amorphous structures is that their physical as well as chemical parameters are better defined and they are more stable. The latter is of particular importance for the substances which in their nature are unstable and sensitive to different ambient influences, such as light, pH, atmosphere and temperature. Pravastatin sodium is particularly sensitive to these negative influences.

It has been known that thus far the sodium salt of pravastatin may only be present in an amorphous form. The Merck Index 1996 describes the sodium salt of pravastatin as an amorphous substance.

Methods for the preparation of the sodium salt of pravastatin described in many patents, for example U.S. Pat. No. 44,537,859, U.S. Pat. No. 4,448,979, U.S. Pat. No. 4,410,629 and U.S. Pat. No. 4,346,227, afford only the preparation of an amorphous form. In the methods disclosed, after separation on the chromatographic columns, the fractions obtained comprising the sodium salt of pravastatin are lyophilized and the sodium salt in a solid—amorphous form is obtained.

The WO-A-98/45410 discloses that after the sodium salt of pravastatin is purified using reverse-phase chromatography, alleged crystals may be obtained by precipitation in the ethanol/ethyl acetate mixture; however, the experiments we have carried out suggest that this combination of the solvents affords the preparation of pravastatin in the amorphous form and not in the crystalline form.

It is an object of the present invention to provide the sodium salt of pravastatin which is improved in purity and stability compared to the salts described in the prior art mentioned above.

Further, it is another object of the present invention to provide a process for the preparation of such a sodium salt of pravastatin.

These and further objects are accomplished by the present invention.

In a first aspect, the present invention provides the sodium salt of pravastatin in a crystalline form. Furthermore, the present invention also provides the sodium salt of pravastatin in a specific crystalline form, wherein the crystals in an X-ray diffraction measurement produce a signal sufficiently comparable to that illustrated in the diffractogram shown in FIG. 2.

In a second aspect, the present invention provides a process for the preparation of the sodium salt of pravastatin in a crystalline form comprising the steps of: (a) dissolution of the sodium salt of pravastatin in a lower aliphatic alcohol; (b) addition of ethyl acetate to the alcoholic solution of the sodium salt of pravastatin; (c) cooling of said alcohol/ethyl acetate mixture; and (d) crystallization.

According to a third aspect of the present invention, there is further provided a pharmaceutical formulation containing the sodium salt of pravastatin in the aforementioned crystalline forms.

The crystalline sodium salt of pravastatin according to the present invention is particularly suitable for the preparation of pharmaceutical products for the treatment of hypercholesterolemia and hyperlipidemia.

In the following, drawings will be briefly described.

FIG. 1: Diffractogram of a conventional amorphous sodium salt of pravastatin which is commercially available, scanned on the X-ray powder diffractometer within 2 to 42° 2θ range with a 0.025° 2θ step and an integration time of 1 second/step.

Figure 2:
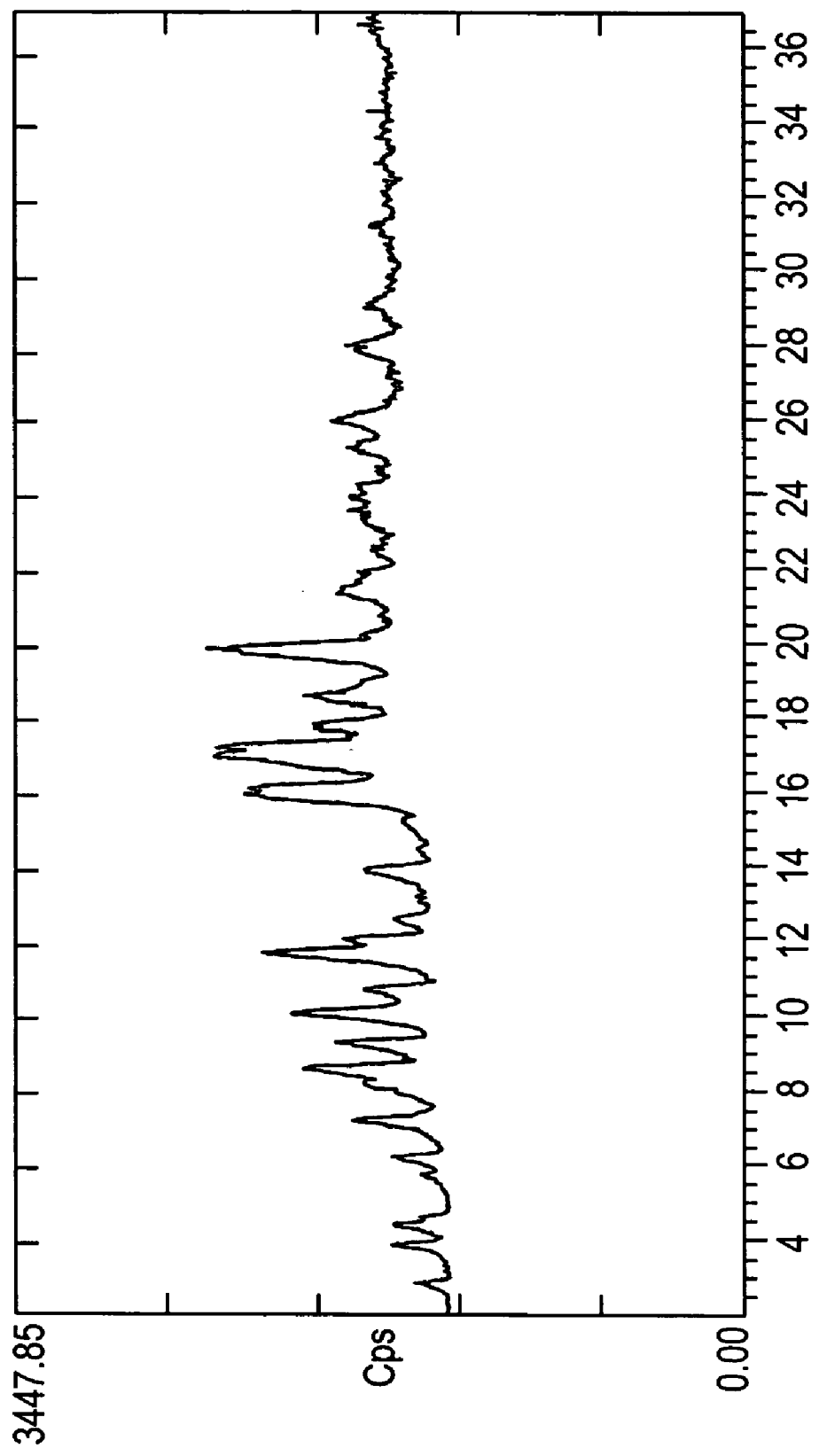

FIG. 2: Diffractogram of crystals of the sodium salt of pravastatin prepared according to Example 2 of the present invention, which are scanned on the X-ray powder diffractometer within 2 to 48° 2θ range with a 0.035° 2θ step and an integration time of 1 second/step.

Figure 3:
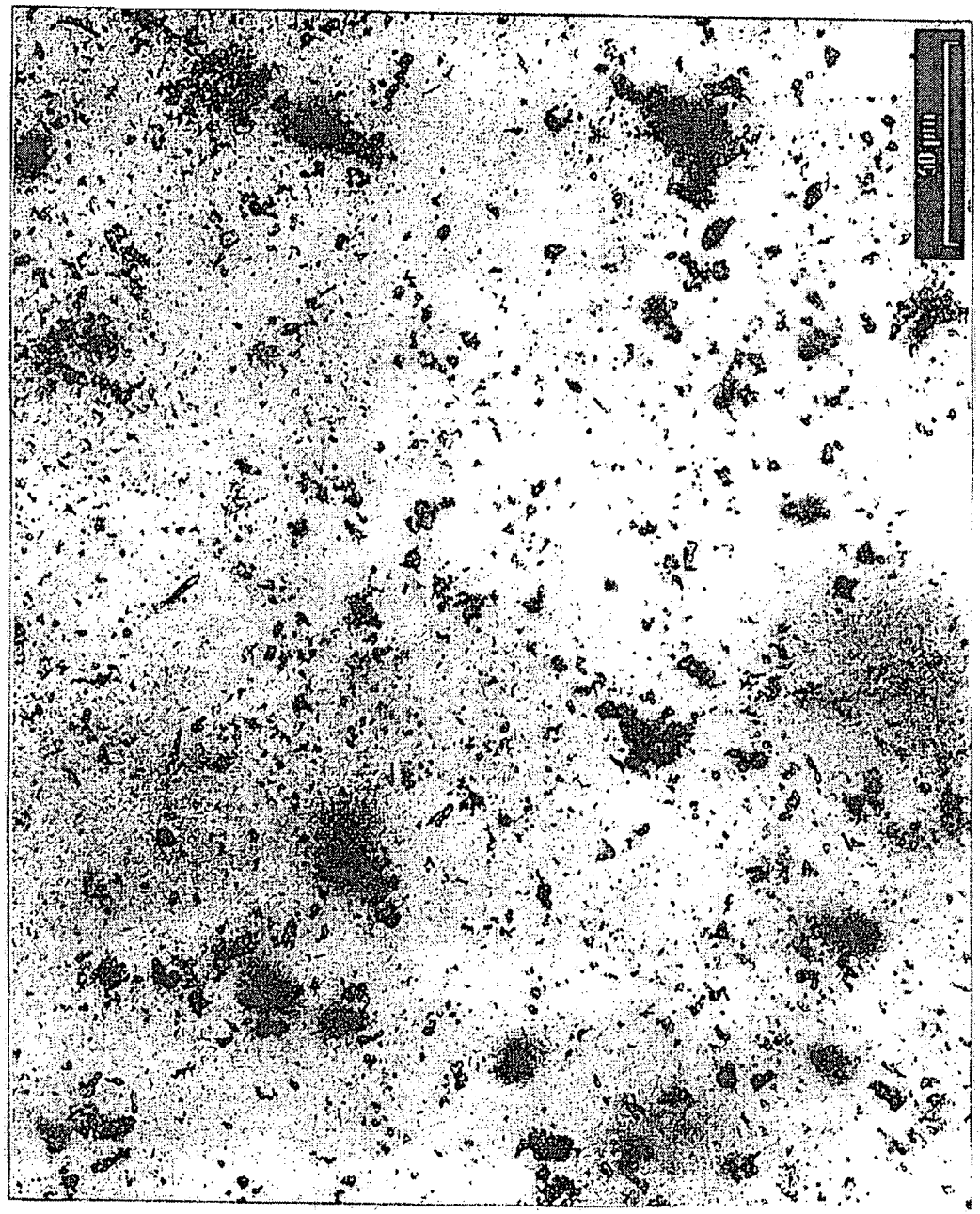

FIG. 3: Image of the amorphous sodium salt of pravastatin used for the X-ray diffraction measurement shown in FIG. 1, which is obtained under the microscope under 400-fold magnification.

Figure 4:
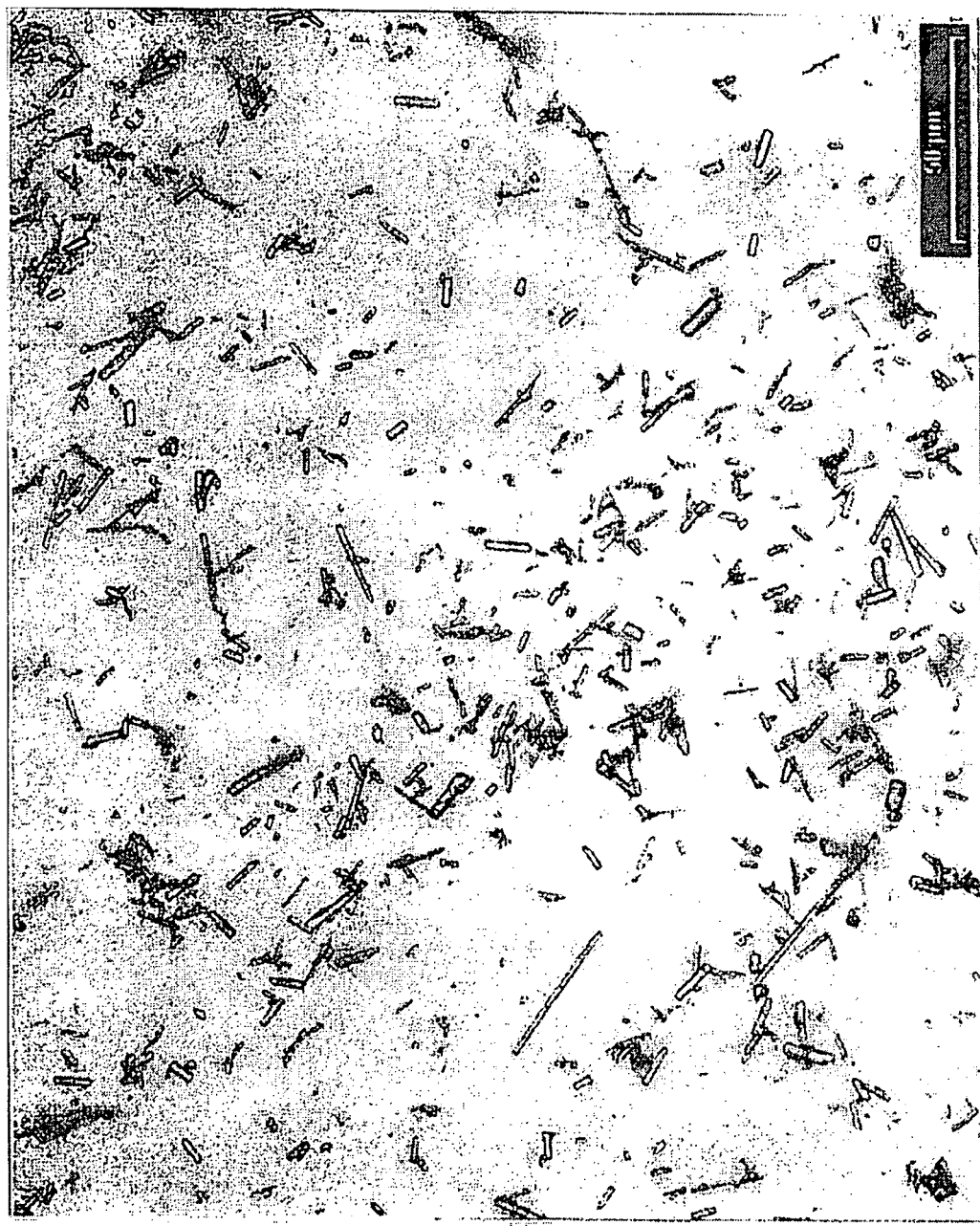

FIG. 4: Image of crystals of the sodium salt of pravastatin prepared according to Example 2 of the present invention, obtained under the microscope under 400-fold magnification.

X-ray diffraction measurements were carried out with a X-ray powder diffractometer (Phillips PW 1710) using a Cu-K$_\alpha$ (20 mA, 40 kV, $\lambda$=1.5406 Å) light source. For microscopic observations, an OLYMPUS BX 50F microscope with a CCD Sonny DXC-950-P camera was used with 400-fold magnification.

In the following, the present invention will be illustrated in more detail by the description of preferred embodiments.

In our research work we have surprisingly found that by suitable selection of the solvents and adequate order of their use the sodium salt of pravastatin in a form having an improved crystallinity, relative to the conventional solid form, can be prepared. Thus, in contrast to the white appearance of the pravastatin sodium solid described in the WO-A-98/45410, it is possible according to the present invention to achieve crystals exhibiting a colorless or pale yellow appearance, which clearly indicates the improved crystallinity and, thus, the clearly crystalline form of the sodium salt of pravastatin provided by the present invention.

Other physical properties of the crystals of the pravastatin sodium of the present invention further indicate the improved crystallinity obtained. Firstly, the crystals according to the present invention can be preferably obtained in the form of needles, sometimes in the form of radiating clusters. Such crystal shape can be readily observed under the microscope, for example when the observation is carried out under 400-fold magnification (see FIG. 4). By contrast, conventionally available amorphous pravastatin sodium appear in the shape of granular particles (see FIG. 3).

Secondly, the melting point of the pravastatin sodium crystals according to the present invention is preferably between 170 and 174° C., more preferably between 172 and 174° C. This melting point range achieved in the present invention is very small for such a complicated chemical structure and confirms the high crystallinity of the pravastatin sodium crystals obtained.

Thirdly, a further characteristic feature of the crystalline pravastatin sodium according to the present invention is that the signal obtained in an X-ray diffraction measurement (Cu-K$_\alpha$, 2$\theta$) have sharp and distinct peaks. In particular, the shape of the X-ray diffraction peaks of pravastatin sodium according to the present invention are defined by a small half-value width, which confirms a high degree of crystallinity. The term "half-value width" means the value of the 2$\theta$-range of one peak at the half height or magnitude of the respective peak. Accordingly, the signals obtained by these measurements comprise distinct peaks (2$\theta$) having a half-value width preferably below 2°, more preferably below 1°, and most preferably below 0,5°

Exemplary crystals of pravastatin sodium prepared according the present invention produce a diffractogram in an X-ray diffraction measurement that is shown in FIG. 2. Due to its particularly improved crystallinity and, thus, purity and stability, such pravastatin sodium crystals which, in an X-ray diffraction measurement (Cu-K), produce a signal sufficiently comparable to that, preferably essentially as that illustrated in the diffractogram shown in FIG. 2, constitute preferred embodiments of the present invention. Unit cells of this crystal could not be determined because of its size and high background at the angles >20° 2$\theta$. Comparison of the recorded diffractogram with the reference from the PDF and CSD databases (PDF—"Powder Diffraction File issued by "International Center for Diffraction Data", 12 Campus Boulevard, Newtown Square, PA 19073-3273 USA; CSD—"Cambridge Structural Database System" issued by "Cambridge Crystallographic Data Centre", 12 Union Road, Cambridge CB2 IEZ, the United Kingdom) has shown that the crystals of the sodium salt of pravastatin according to the present invention are really a novel and thus only known crystalline form of the sodium salt of pravastatin. For comparison, a diffractogram of amorphous pravastatin sodium which is commercially available is shown in FIG. 1.

The process for the preparation of crystals according to the present invention as described above comprises the following steps:

(a) Providing a solution containing pravastatin and sodium cations in a lower aliphatic alcohol. This is suitably carried out by dissolution of an solid and/or amorphous sodium salt of pravastatin in a lower aliphatic alcohol having preferably 1 to 4 carbon atoms. More preferably, the alcohol used for the dissolution of pravastatin sodium is ethanol or methanol. The best crystallization results have been achieved when preparing a solution of pravastatin sodium in methanol.

(b) Addition of ethyl acetate into the alcoholic solution, preferably while the alcoholic solution obtained in step (a) is stirred continually. The addition of ethyl acetate into the alcoholic solution of pravastatin sodium is preferably carried out slowly, while the addition may be continuously or stepwise.

(c) Cooling of the resulting alcohol/ethyl acetate mixture.

(d) Crystallization.

In step (d), from the cooled mixture crystals of the sodium salt of pravastatin, which preferably have a colorless or pale yellow appearance and are in the form of needles or radiating clusters, are formed.

Additionally, the crystals obtained by this process may preferably be filtered, ethyl acetate washed and dried.

The crystallization is carried out advantageously if the initial concentration of the sodium salt of pravastatin in the aliphatic alcohol used for the dissolution is preferably between 0.03 and 0.3 g/ml, more preferably between 0.05 and 0.2 g/ml, particularly about 0.1 g/ml, and if the volume of added ethyl acetate in step (b) does preferably not exceed the 15-fold volume, more preferably the 10-fold volume of the starting solution of the sodium salt of pravastatin in the aliphatic alcohol.

Furthermore, to achieve a higher crystallization rate, the preferred temperature of crystallization is below 15° C., more preferably below 10° C., particularly about 8° C. or enforcing further crystallization, it is preferred to carry out the process according to the invention with additional steps of:

(e) Further adding ethyl acetate to the mixture of step (d). This is done after an appropriate period of a first crystallization stage where crystallization occurs.

(f) then, crystallization of pravastatin sodium is continued while cooling.

With such an additional crystallization stage the yield of crystalline pravastatine sodium can be increased, normally by 5 to 10%.

The volume of ethyl acetate additionally added to the cooled mixture in step (e) is preferably in the range of from 25 to 75% by volume, more preferably from 40 to 60% by volume based on the volume of ethyl acetate added in step (b).

Furthermore, the crystals are preferably formed within a total crystallization time of 3 to 20 hours. More preferably, the total crystallization time is between 4 and 12 hours, particularly about 4 hours.

The present invention also relates to pharmaceutical formulations containing the sodium salt of pravastatin in the form of crystals. The pharmaceutical formulation is present in the form which is suitable for oral and parenteral administration, respectively, and is useful for the treatment of hypercholesterolemia and hyperlipidemia. The pharmaceutical formulation of the present invention is available in the form of tablets, capsules, granules and suppositories as well as in the form of suspensions.

The pharmaceutical formulation of this invention may comprise, in addition to the sodium salt of pravastatin, one or more fillers, such as microcrystalline cellulose, lactose, sugars, starches, modified starch, mannitol, sorbitol and other polyols, dextrin, dextran and maltodextrin, calcium carbonate, calcium phosphate and/or hydrogen phosphate, sulphate, one or more binders, such as lactose, starches, modified starch, dextrin, dextran and maltodextrin, microcrystalline cellulose, sugars, polyethylene glycols, hydroxypropyl cellulose, hydroxypropyl methylcellulose, ethylcellulose, hydroxyethyl cellulose, methylcellulose, carboxymethyl cellulose, gelatin, acacia gum, tragacanth, polyvinylpyrrolidone, magnesium aluminium silicate, one or more disintegrating agents such as croscarmellose sodium, cross-linked polyvinylpyrrolidone, cross-linked carboxymethyl starch, starches and microcrystalline cellulose, magnesium aluminium silicate, polyacrylin potassium, one or more different glidants such as magnesium stearate, calcium stearate, zinc stearate, calcium behenate, sodium stearyl fumarate, talc, magnesium trisilicate, stearic acid, palmitic acid, carnauba wax, silicon dioxide, one or more buffering agents such as sodium or potassium citrate, sodium phosphate, dibasic sodium phosphate, calcium carbonate, hydrogen phosphate, phosphate, sulphate, sodium or magnesium carbonate, sodium ascorbinate, benzoate, sodium or potassium hydrogen carbonate, lauryl sulphate, or mixtures of such buffering agents.

If required any, the formulation may also comprise surfactants and other conventional components for solid, pharmaceutical formulations such as coloring agents, lakes, aromas and adsorbents. As surfactants the following may be used: ionic surfactants, such as sodium lauryl sulphate or non-ionic surfactants such as different poloxamers (polyoxyethylene and polyoxypropylene copolymers), natural or synthesized lecithins, esters of sorbitan and fatty acids (such as Span®, manufactured by Atlas Chemie), esters of polyoxyethylenesorbitan and fatty acids (such as Tween®, manufactured by Atlas Chemie), polyoxyethylated hydrogenated castor oil (such as Cremophor®, manufactured by BASF), polyoxyethylene stearates (such as Brij®, manufactured by Atlas Chemie), dimethylpolysiloxane or any combination of the above mentioned surfactants.

If the solid pharmaceutical formulation is in the form of coated tablets, the coating may be prepared from at least one film-former such as hydroxypropyl methylcellulose, hydroxypropyl cellulose, at least from one plasticizer such as polyethylene glycols, dibutyl sebacate, triethyl citrate, and other pharmaceutical auxiliary substances conventional for film coatings, such as pigments, fillers and others.

The pharmaceutical formulation can be prepared by conventional formulation methods known to those skilled in the art.

The present invention is illustrated but by no means limited by the following examples.

EXAMPLE 1

The sodium salt of pravastatin (1 g) was dissolved in methanol (10 ml) and while stirring ethyl acetate was added. The resulting clear yellow solution was cooled to 8° C. and allowed to stand overnight. Formed radiating clusters of thin, long needle-like crystals were filtered, washed with ethyl acetate (20 ml) and dried. Yield: 0.87 g of pale yellow crystals, melting point 172–174° C.

EXAMPLE 2

The sodium salt of pravastatin (2 g) was dissolved in methanol (20 ml) and while stirring ethyl acetate (80 ml) was added. The clear, slightly yellow solution was cooled to 8° C. and allowed to stand for 4 hours. Formed radiating clusters of thin, long needle-like crystals were filtered, washed with ethyl acetate (20 ml) and dried. Yield: 1.53 g of colorless crystals, melting point 172–174° C.

EXAMPLE 3

The sodium salt of pravastatin (2 g) was dissolved in methanol (20 ml) and while stirring ethyl acetate (150 ml) was added. The resulting clear, slightly yellow solution was cooled to 8° C. and allowed to stand for 4 hours. Formed radiating clusters of thin, long needle-like crystals were filtered, washed with ethyl acetate (20 ml) and dried. Yield: 1.66 g of colorless crystals, melting point 172–174° C.

EXAMPLE 4

The sodium salt of pravastatin (2 g) was dissolved in methanol (20 ml) and while stirring ethyl acetate (170 ml) was added. The resulting clear, slightly yellow solution was cooled to 8° C. and allowed to stand for 4 hours. Formed radiating clusters of thin, long needle-like crystals were filtered, washed with ethyl acetate (20 ml) and dried. Yield: 1.75 g of colorless crystals, melting point 172–174° C.

EXAMPLE 5

The sodium salt of pravastatin (2 g) was dissolved in methanol (12 ml) and while stirring ethyl acetate (100 ml) was added. The resulting clear, slightly yellow solution was cooled to 8° C. and allowed to stand for 1 hour. After that further ethyl acetate (60 ml) was added, so the pravastatin still dissolved in the solution was forced to crystallize. After 2 hours at 8° C. the formed radiating clusters of thin, long needle-like crystals were filtered, washed with ethyl acetate (20 ml) and dried. Yield: 1.85 g of colorless crystals, melting point 172–174° C.

The invention claimed is:

1. The sodium salt of pravastatin in a crystalline form wherein the crystals in the X-ray diffraction measurement produce distinct peaks having a half-value width below 2° measured at the reflection angle 2θ using $CuK_\alpha$ radiation.

2. The sodium salt of pravastatin according to claim 1, wherein the melting point is in the range of from 170° C. to 174° C.

3. A process for preparing pharmaceutical products for the treatment of hypercholesterolemia and hyperlipidemia comprising the step of adding the active agent pravastatin as a crystalline sodium salt together with a pharmaceutically acceptable carrier; wherein the crystals in the X-ray diffraction measurement produce distinct peaks having a half-value width below 2° measured at the reflection angle 2θ using $CuK_\alpha$ radiation.

4. A process for the preparation of the sodium salt of pravastatin in crystalline form, comprising the steps of:
   (a) first preparing a solution of pravastatin and sodium cations in a lower aliphatic alcohol;

(b) thereafter adding ethyl acetate to said alcoholic solution so as to obtain a clear solution of the pravastatin, sodium cations, aliphatic alcohol and ethyl acetate;

(c) thereafter cooling said clear alcohol/ethyl acetate mixture of step (b); and (d) obtaining said sodium salt of pravastatin in crystalline form; wherein the crystals in the X-ray diffraction measurement produce distinct peaks having a half-value width below 2° measured at the reflection angle 2θ using CuK$_\alpha$ radiation.

5. The process according to claim 4, wherein the lower aliphatic alcohol is ethanol or methanol.

6. The process according to claim 4, wherein the ethyl acetate is added while the alcoholic solution of the sodium salt of pravastatin is stirred continually.

7. The process according to claim 4, wherein the concentration of the sodium salt of pravastatin in the alcoholic solution of step (a) is between 0.03 and 0.3 g/mL.

8. The process according to claim 4, wherein the volume of added ethyl acetate in step (b) does not exceed the 15-fold volume of the initial alcoholic solution of the sodium salt of pravastatin.

9. The sodium salt of pravastatin in crystalline form having an X-ray diffraction pattern comprising characteristic peaks at 4.0±0.2; 10.2±0.2; 16.3±0.2; 17.4±0.2 and 20.0±0.2 degrees measured at reflection angle 2θ.

10. The sodium salt of pravastatin in a crystalline form having an X-ray diffraction pattern comprising characteristic peaks at 4.0±0.2; 6.3±0.2; 10.2±0.2; 16.3±0.2; 17.4±0.2; 18.0±0.2 and 20.0±0.2 degrees measured at reflection angle 2θ.

11. The sodium salt of pravastatin in a crystalline form having an X-ray diffraction pattern comprising characteristic peaks at 4.0±0.2; 6.3±0.2; 10.2±0.2; 11.8±0.2; 16.3±0.2: 17.4±0.2; 18.0±0.2 and 20.0±0.2 degrees measured at reflection angle 2θ.

12. The crystalline form of the sodium salt of pravastatin having an X-ray diffraction pattern comprising characteristic peaks at 4.0±0.2; 10.2±0.2; 16.1±0.2 (broad); 17.2±0.2 (broad); and 20.0±0.2.

13. The crystalline form of the sodium salt of pravastatin of claim 12 wherein the broad peak at 16.1±0.2 comprises a peak at 16.05 and at 16.3 and the broad peak at 17.2±0.2 comprises a peak at 17.0 and 17.3.

14. The process according to claim 4, wherein the concentration of the sodium salt of pravastatin in the alcoholic solution of step (a) is between 0.05 and 0.2 g/mL.

15. The process according to claim 4, wherein the concentration of the sodium salt of pravastatin in the alcoholic solution of step (a) is about 0.1 g/mL.

16. The process according to claim 4, wherein the volume of added ethyl acetate in step (b) does not exceed the 10-fold volume of the initial alcoholic sodium of the sodium salt of pravastatin.

17. The process according to claim 4 additionally comprising after a first crystallization stage the steps of:

(e) adding further ethyl acetate to the alcohol/ethyl acetate mixture; and (f) causing further crystallization.

18. The process according to claim 4, wherein the lower aliphatic alcohol is methanol.

19. The process according to claim 4, wherein the concentration of the sodium salt of pravastatin in the alcoholic solution of step (a) is between 0.03 and 0.3 g/mL.

20. The process according to claim 17, wherein the volume of further added ethyl acetate in step (e) is in the range of from 25 to 75% by volume based on the volume of ethyl acetate added in step (b).

21. The process according to claim 4, wherein the alcohol/ethyl acetate mixture is cooled to a temperature below 15° C.

22. The process according to claim 4, wherein the total crystallization time is between 3 and 20 hours.

23. The process according to claim 4, wherein the formed crystals are filtered, washed with ethyl acetate and dried.

* * * * *